United States Patent [19]

Babiec, Jr. et al.

[11] 3,941,822

[45] Mar. 2, 1976

[54] PROCESS FOR THE PREPARATION OF METHYLENE-BRIDGED DIARYL ISOCYANATES

[75] Inventors: John S. Babiec, Jr., Orange; Wilhelm J. Schnabel, Branford, both of Conn.

[73] Assignee: Olin Corporation, New Haven, Conn.

[22] Filed: Oct. 3, 1974

[21] Appl. No.: 511,589

[52] U.S. Cl. .................. 260/453 P; 260/453 AM
[51] Int. Cl.² ............ C07C 118/00; C07C 119/048
[58] Field of Search ............... 260/453 P, 453 AM

[56] References Cited
UNITED STATES PATENTS
3,255,226  6/1966  McShane, Jr. .................. 260/453

*Primary Examiner*—Lewis Gotts
*Assistant Examiner*—Dolph H. Torrence
*Attorney, Agent, or Firm*—James B. Haglind; Donald F. Clements; T. P. O'Day

[57] ABSTRACT

A process for the production of methylene-bridged diaryl isocyanates by the reaction of α-halomethyl aromatic compounds with aromatic isocyanates in the presence of a catalyst. The catalyst comprises a metal salt of an aliphatic or cycloaliphatic organic acid where the metal is zinc, cadmium or mercury.

Methylene-bridged diaryl isocyanates are suitably used in the production of polyurethane elastomers and foams.

12 Claims, No Drawings

PROCESS FOR THE PREPARATION OF METHYLENE-BRIDGED DIARYL ISOCYANATES

This invention relates to the preparation of methylene-bridged diaryl isocyanates by the reaction of α-halomethyl acromatic compounds with aromatic isocyanates in the presence of a metal salt of an aliphatic or cycloaliphatic organic acid as catalyst.

The prior art teaches the preparation of methylene-bridged diaryl isocyanates, for example, by the reaction of haloalkyl aryl isocyanates with reactive aromatic compounds in the presence of a Friedel-Crafts catalyst as described in U.S. Pat. No. 3,255,226, June 7, 1966 issued to H. F. McShane, Jr. This process requires the Friedel-Crafts catalyst to be added to the reaction mixture at the lowest possible temperature. In order to maintain an efficient reaction rate during the preparation of the methylene-bridged diaryl isocyanates, it is often necessary to add further amounts of catalyst to the reaction mixture. Using the process of U.S. Pat. No. 3,255,226, this requires the interruption of the reaction by cooling the reaction mixture to a temperature where the addition of make up amounts of catalyst avoids a spontaneous violent reaction. Further, the process of U.S. Pat. No. 3,255,226 produces significant amounts of undesirable by-products by promoting the condensation of the reactive aromatic compounds with the methylene-bridged diaryl isocyanates formed.

Therefore, it is an object of the present invention to provide an improved catalyst for the preparation of methylene-bridged diaryl isocyanates.

It is a further object of the present invention to provide a process for the preparation of methylene-bridged diaryl isocyanates having reduced amounts of undesirable by-products.

These and other objects of the invention are accomplished in a process for preparing methylene-bridged diaryl isocyanates by reacting an α-halomethyl aromatic compound with an aromatic isocyanate in the presence of selected metal salts of aliphatic and cycloaliphatic organic acids.

The catalysts of the improved process of the present invention are metal salts of aliphatic and cycloaliphatic acids wherein the metal is zinc, cadmium or mercury, the zinc and cadmium salts being preferred. The organic acid moiety in the catalysts of the invention contains 1–20, and preferably 1–18, carbons in the case of the aliphatic acid salts and 4–20, and preferably 4–14, carbons in the case of the cycloaliphatic acid salts.

Typical examples of metal salts of aliphatic acids suitable for use as catalysts in the improved process of the present invention include:
zinc formate
mercurous formate
mercuric acetate
cadmium acetate
zinc propionate
zinc butyrate
cadmium hexanoate
zinc decanoate
zinc laurate
cadmium laurate
zinc palmitate
cadmium stearate
zinc neodecanoate Suitable examples of metal salts of cycloaliphatic acids employable as catalysts include:
zinc naphthenate
mercuric cyclobutanecarboxylate
cadmium naphthenate
zinc cyclododecanecarboxylate
mercuric cyclohexaneacetate The catalysts described above are used in an improved process for the preparation of methylene-bridged diaryl isocyanates in which one reactant is an α-halomethyl aromatic compound. Any compound having an α-halomethyl group substituted on an aromatic ring may be employed. However, those α-halomethyl aromatic compounds are preferred in which the halogen is chlorine or bromine and further in which the aromatic moiety is a substituted or unsubstituted phenyl or naphthyl. The substituents include, for example, chlorine, bromine, alkyl of 1 to 4 carbons, NCO, and mixtures thereof.

Typical examples of α-halomethyl aromatic compounds which may be employed include:
Benzyl chloride
Benzyl bromide
Benzal chloride
2-Chlorobenzyl chloride
4-Chlorobenzyl chloride
4-Bromobenzyl chloride
α-Bromoxylene
4-Xlylene dichloride
α-Chloromethylnapthalene
5-Chloro-1-chloromethylnaphthalene
α-Chloro-4-toluene isocyanate
α-Chloro-2,4-toluene diisocyanate
5,α-dichloro-2,4 toluene diisocyanate
5-Chloromethyl-1-naphthylisocyanate
5-Bromo-1-chloromethylnaphthalene
α,α-Dichloro-2,4 toluene diisocyanate
3,5,α-trichloro-2,4-toluene diisocyanate
3,5,6α-tetrachloro-2,4 toluene diisocyanate
α,α,α', α',-Tetrachloro-p-xylene
α-chloro-2,4-/2,6-toluene diisocyanate (isomer mixture)
5,α-dichloro-2,4-/2,6toluene diisocyanate (isomer mixture)

Particularly preferred α-halomethyl aromatic compounds for use in the process of the invention are benzyl chloride, o-chlorobenzyl chloride, benzal chloride, and α-chloro-2,4- and 2,6-toluene diisocyanate (isomer mixture).

The second reactant in the improved process of the present invention is an aromatic isocyanate. Any such compound may be employed such as disclosed in U.S. Pat. No. 3,255,226, the entire disclosure of which is incorporated by reference herein. However, it is preferred to employ those aromatic isocyanates in which the aromatic moiety is phenyl or naphthyl. Illustrative such compounds include:
Phenyl isocyanate
o-Chlorophenyl isocyanate
2-toluene isocyanate
2,4-toluene diisocyanate
2,6-toluene diisocyanate
3-chloro-2,6-toluene diisocyanate
2,4-/2,6-toluene diisocyanate (isomer mixture)
1-naphthylisocyanate
Naphthalene-1,5-diisocyanate
m-Phenylene diisocyanate
p-Phenylene diisocyanate Toluene diisocyanates and substituted toluene diisocyanates are especially preferred aromatic isocyanates for use in the process of the invention. Isomers of toluene diisocyanate, and mixtures thereof, wherein the isocyanate groups therein occupy positions which are meta or para to each other on the aromatic ring are most preferred.

In carrying out the improved process of the present invention of preparing methylene-bridged diaryl isocyanates, at least one mole of the aromatic isocyanate compound should be employed for each α-halogen contained in a mole of the α-halomethyl aromatic compound. Thus, in the case of α-halomethylaromatic compounds having only one α-halogen, at least one mole of aromatic isocyanate compound should be used per mole of α-halomethyl aromatic compound. With compounds such as benzal chloride, which contains two α-halogens per mole, at least two moles of aromatic isocyanate compound should be employed per mole of α-halomethylaryl compound. The yield of methylene-bridged diaryl isocyanate generally will be higher if the aromatic isocyanate compound is employed in excess. This is true because α-halomethylaromatic compounds with open positions on their ring are often capable of condensing with themselves and the presence of a large excess of aromatic isocyanate compound reduces the tendency of this undesirable side-reaction to occur. Excessive aromatic isocyanate compound also reduces the probability of two molecules of the α-halomethylaromatic compound reacting with the same molecule of aromatic isocyanate compound. By employing about 3–5 moles of aromatic isocyanate compound per equivalent of α-halogen in a mole of the α-halomethylaromatic compound, the self-condensation of the α-halomethylaromatic compound and the dialkylation of the aromatic isocyanate compound can be suppressed sufficiently so that a good yield of the desired monomeric rather than polymeric methylene-bridged diaryl isocyanate is obtained. Even greater quantities of aromatic isocyanate compound may be employed if so desired, but the advantages gained through a slight improvement in yield or quality are usually offset by the need to recover large quantities of the aromatic isocyanate compound.

The metal salts of aliphatic and cycloaliphatic organic acids employed as catalysts may be added to the reaction mixture in any suitable catalytic amount such as from about 0.5 to about 20, and preferably from about 1 to about 10 mole percent based on the combined molar amounts of α-halomethyl aromatic compound and aromatic isocyanate compound present in the reaction mixture.

The entire amount of catalyst may be added to the reaction mixture prior to initiating the reaction or the total amount of catalyst may be added in portions to the reaction mixture during the course of the reaction. It is unnecessary to interrupt the reaction, for example, by cooling down the reaction mixture when adding further portions of catalyst.

The process of the present invention for preparing methylene-bridged diaryl isocyanates may be carried out at temperatures ranging from about 100° to about 250° C. Selection of the temperature depends upon such factors as the quantity of catalyst, the reactivity of the halomethylaromatic compound and the aromatic isocyanate compound, and the boiling and freezing points of the reaction system. Preferred are temperatures in the range of from about 120° to about 180° C. Temperatures above 250° C. are generally not employed because the rate of thermal decomposition of the desired isocyanate may become excessive at such high temperatures. Naturally, the temperature of the condensation reaction cannot exceed the boiling point of the system without adding the complication of pressurizing the system.

The time required to complete the condensation reaction involved in this process usually ranges from about 2 to about 20 hours depending on several factors including the catalyst employed, the temperature of reaction and the nature of the starting materials.

The improved process of the present invention may be carried out in the presence of solvent, if desired. Solvents may be useful when the reactants or the methylene-bridged diaryl isocyanate products are high melting solids. Solvents may also be useful in adding additional amounts of catalyst to the reaction mixture when the process is conducted continuously. It will be understood that a solvent should be selected which is inert to the reactants and the catalyst and does not interfere with the reaction. Suitable solvents include halogenated aliphatic and aromatic compounds such as tetrachloroethane, trichlorobenzene, tetrachlorobenzene, as well as nitrobenzene.

The improved process of the present invention is a condensation reaction where the α-halomethylaromatic compound is condensed with the aromatic isocyanate compound accompanied by the production of hydrogen chloride. If the condensation is carried out at temperatures below about 125° C., a significant quantity of this hydrogen chloride may be combined with isocyanato groups to produce carbamyl chlorides. This undesirable side reaction can be minimized by sparging the reaction mixture with a dry inert gas during the reaction. At higher temperatures sparging of the reaction mixture with a slow stream of an inert gas is still advantageous as hydrogen chloride will be removed about as rapidly as it is evolved.

The evolution of hydrogen chloride during the reaction provides an indication of the extent of conversion of the α-halomethyl aromatic compound. For example, HCl is evolved in the reaction of benzyl chloride with a commercial mixture of 2,4- and 2,6-toluene diisocyanate in the condensation reaction to produce diisocyanatotolyl phenyl methane. In addition, HCl is evolved when a portion of the benzyl chloride is converted to undesirable by-product tars. Employing the metal salts of aliphatic and cycloaliphatic organic acids as catalysts, this undesirable conversion to by-products is considerably reduced. When employing the catalysts defined above in the prescribed amounts, a moderate conversion rate of the α-halomethyl aromatic compound as indicated by HCl formation occurs, however, the yield of methylene-bridged diaryl isocyanate based on this conversion is high. Thus, the amount of α-halomethyl aromatic compound converted to undesired by-product tars in proportion to the amount reacted to form the desired product is low. Where the methylene-bridged diaryl isocyanate is produced in a continuous process, the amount of α-haloalkyl aromatic compound which must be continually added to the reaction mixture is greatly reduced making the process cheaper to run. In addition, the isolation of the desired methylene-bridged diaryl isocyanate is simplified as the quantity of by-product tars with which it is mixed is significantly lowered.

The methylene-bridged diaryl isocyanates produced by the improved process of the present reaction may be recovered by distillation at reduced pressure, for example, pressures of less than 1 mm. Hg and preferably from about 0.05 to about 0.1 mm Hg. The methylene-bridged diaryl isocyanate products may also be extracted from the reaction mixture using a solvent such as heptane or petroleum ether.

Where the product is used, for example, in the preparation of rigid polyurethane foams, it is sufficient to remove the α-halomethyl aromatic compound and the aromatic isocyanate compound from the reaction mixture, and further separation of the methylene-bridged diaryl isocyanates from the catalyst or by-products is unnecessary.

The methylene-bridged diaryl isocyanates produced by the present invention are colorless liquids or solids. They are capable of undergoing all of the usual reactions which are characteristic of aromatic isocyanates. Because of their extremely high boiling points, the methylene-bridged diaryl isocyanates exhibit low vapor pressures at normal temperatures and can be safely handled without special ventillation which is often required with more volatile isocyanates.

The methylene-bridged diaryl monoisocyanates may be employed in any of the usual applications for aromatic monoisocyanates such as treating wool and cellulose fibers to modify the properties, treating papers or latex impregnated paper to increase wet strength, capping oxymethylene polymers, removing active hydrogen impurities from petroleum products and assisting in bonding a variety of plastic or elastic materials to fibers containing reactive hydrogen.

The methylene-bridged diaryl polyisocyanates which may be produced by the improved process of this invention are, for example, of utility in the preparation of polyurethane elastomers and foams.

The following examples, in which parts and percentages are by weight unless otherwise specified, are illustrative of the improved process of the present invention for preparing methylene-bridged diaryl isocyanates.

EXAMPLE 1

In a reaction vessel, equipped with a thermometer, a stirrer, a reflux condenser and a nitrogen gas inlet tube, were placed 1 mole of benzyl chloride, 0.05 mole of zinc laurate and 5 moles of an 80/20 by weight isomer mixture of 2,4-/2,6-toluene diisocyanate. The agitated mixture was heated to 160° C. while a slow stream of dry nitrogen gas was passed through it. Hydrogen chloride, which was evolved during the reaction, was removed with the out-flowing nitrogen gas stream, and it was subsequently captured in a separate vessel where it was absorbed in water. When the evolution of hydrogen chloride decreased substantially, an additional 0.0125 mole of zinc laurate was added while maintaining the reaction temperature constant. Evolution of HCl initially increased and when this evolution had subsided a second addition of 0.0125 mole of zinc laurate was made. After a total reaction time of about 18 hours, the evolution of HCl had practically ceased and the reaction mixture was cooled to room temperature and extracted with petroleum ether. After stripping the extraction solvent, the remaining liquid was subjected to a fractional vacuum distillation. The conversion of benzyl chloride, as determined by the condensation and titration of HCl with a base, amounted to 59 percent of the amount initially charged. Pure diisocyanatotolyl phenyl methane, distilling at 165°–170° (0.5–0.75 mm) was obtained in a yield of 79 percent of theory (based on the conversion of benzyl chloride).

The identity and structure of diisocyanatotolyl phenyl methane was confirmed by mass spectrometry (MS), nuclear magnetic resonance (NMR), and vapor phase chromatography (VPC).

EXAMPLE 2

To a reaction vessel equipped with a thermometer, a stirrer, a reflux condenser and a nitrogen gas inlet tube was added 1 mole of benzyl chloride, 5 moles of commercial toluene diisocyanate (an 80/20 by weight isomer mixture of 2,4-/2,6-toluene diisocyanate) and 0.1 moles of zinc propionate. The reaction flask was heated to 150°–180° C. while passing a stream of dry N₂ through the agitated reaction mixture. When the evolution of HCl had essentially ceased, after about 10 hours, the reaction mixture was cooled to room temperature and extracted with petroleum ether. The product work up procedure used in Example 1 was repeated. The conversion of benzyl chloride amounted to 42 percent of the amount initially added. Pure diisocyanatotolyl phenyl methane was obtained in 87 percent yield (based on the conversion of benzyl chloride).

EXAMPLES 3–6

The procedure of Example 2 was repeated using zinc naphthenate, zinc laurate, cadmium stearate and zinc formate in place of zinc propionate. Results for Examples 3–6 are given in Table I below.

COMPARATIVE EXAMPLES 1–2

The procedure of Example 2 was repeated employing zinc chloride and aluminum chloride instead of zinc propionate. Results for comparative examples 1 and 2 (C1 and C2) are given in Table I below.

The results of Table I show that, using metal salts of aliphatic and cycloaliphatic organic acids as catalysts gives yields of the desired product which are substantially higher than when using the inorganic salts of the prior art. In addition, the conversion of benzyl chloride to undesirable by-products is considerably reduced.

EXAMPLE 7

The procedure of Example 2 was used to prepare o-chlorophenyl diisocyanatotolyl methane, using 1 mole of o-chlorobenzyl chloride instead of 1 mole of benzyl chloride and 0.1 mole of zinc formate in place of 0.1 mole of zinc propionate as used in Example 2. The product was a colorless liquid which distilled at 180°–182° C. at 0.5–1.0 mm. of mercury pressure. The structure and identity of o-chlorophenyl diisocyanatotolyl methane was confirmed by MS, NMR and VPC.

Table I

| Example No. | Catalyst | Percent Conversion of Benzyl Chloride | Percent Yield of Diisocyanatotolyl Phenyl Methane | Reaction Time (hrs.) |
| --- | --- | --- | --- | --- |
| 3 | zinc naphthenate | 51 | 79 | 10 |
| 4 | zinc laurate | 40 | 73 | 16 |
| 5 | cadmium stearate | 48 | 58 | 16 |

Table I-continued

| Example No. | Catalyst | Percent Conversion of Benzyl Chloride | Percent Yield of Diisocyanatotolyl Phenyl Methane | Reaction Time (hrs.) |
|---|---|---|---|---|
| 6 | zinc formate | 60 | 50 | 2 |
| C1 | zinc chloride | 99 | 39 | 2 |
| C2 | aluminum chloride | 91 | 50 | 6 |

EXAMPLE 8

The procedure of Example 2 was used to prepare diisocyanatophenyl isocyanatophenyl methane by the reaction of 1 mole of α-chlorotoluene diisocyanate (prepared from an 80/20 by weight isomer mixture of 2,4-/2,6-toluene diisocyanate) with 5 moles of phenyl isocyanate in the presence of 0.1 mole of zinc laurate. The conversion of α-chlorotoluene diisocyanate was 65 percent of the amount initially reacted. The product, a colorless liquid which distilled at 170°–175° C. at 0.05 to 0.1 mm Hg. was obtained in a yield of 20 percent (based on the conversion of α-chlorotoluene diisocyanate).

What is claimed is:

1. In a process for preparing methylene-bridged diaryl isocyanates by reacting an α-halomethyl aromatic compound with an aromatic isocyanate at a temperature in the range of from about 100° to about 250° C., and in the presence of a catalyst, the improvement which comprises employing as said catalyst a zinc, cadmium or mercury salt of an aliphatic carboxylic acid having 1–20 carbon atoms or a cycloaliphatic carboxylic acid having 4–20 carbon atoms.

2. The process of claim 1 in which said metal is zinc or cadmium.

3. The process of claim 2 in which the halogen of said α-halomethyl aromatic compound is chlorine or bromine.

4. The process of claim 3 in which said aromatic group in said α-halomethyl aromatic compound is phenyl or naphthyl and said aromatic group in said aromatic isocyanate is phenyl or naphthyl.

5. The process of claim 4 in which from about 3–5 moles of said aromatic isocyanate are employed per each α-halogen in a mole of said α-halomethylaromatic compound.

6. The process of claim 5 in which said catalyst is employed in an amount of from about 0.5 to about 20 mole percent of the combined molar amounts of said α-halomethyl aromatic compound and said aromatic isocyanate present in the reaction mixture.

7. The process of claim 6 in which said α-halomethyl aromatic compound is selected from the group consisting of benzyl chloride, o-chlorobenzyl chloride and α-chlorotoluene diisocyanate and said aromatic isocyanate is selected from the group consisting of phenyl isocyanate and toluene diisocyanate.

8. The process of claim 7 in which said catalyst is selected from the group consisting of zinc formate, zinc propionate, zinc laurate, cadmium stearate and zinc naphthenate.

9. The process of claim 8 in which said temperature is in the range of from about 120° to about 180° C.

10. In a process for preparing methylene-bridged diaryl isocyanates by reacting in an α-halomethyl aromatic compound with an aromatic isocyanate at a temperature in the range of from about 100° to about 250°C., and in the presence of a catalyst, the improvement which comprises employing as said catalyst a zinc, cadmium, or mercury salt selected from the group consisting of formate, acetate, propionate, butyrate, hexanoate, decanoate, laurate, palmitate, stearate, neodecanoate, naphthenate, cyclobutanecarboxylate, cyclododecanecarboxylate, and cyclohexaneacetate.

11. The process of claim 10 in which said salt is selected from the group consisting of formate, propionate, laurate, stearate, and naphthenate.

12. The process of claim 11 in which said catalyst is selected from the group consisting of zinc formate, zinc propionate, zinc laurate, cadmium stearate and zinc naphthenate.

* * * * *